(12) United States Patent  
Joerger et al.

(10) Patent No.: US 7,314,311 B2  
(45) Date of Patent: Jan. 1, 2008

(54) METHOD FOR TESTING THE QUALITY OF A DETECTOR MODULE FOR AN X-RAY COMPUTER TOMOGRAPH

(75) Inventors: Clemens Joerger, Forchheim (DE); Quirin Spreiter, Erlangen (DE); Thomas Von Der Haar, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 54 days.

(21) Appl. No.: 11/288,377

(22) Filed: Nov. 29, 2005

(65) Prior Publication Data  
US 2006/0120514 A1    Jun. 8, 2006

(30) Foreign Application Priority Data  
Nov. 30, 2004    (DE)    ............... 10 2004 057 741

(51) Int. Cl.  
*G01D 18/00* (2006.01)
(52) U.S. Cl. ............ 378/207; 378/19; 250/252.1
(58) Field of Classification Search .......... 378/4, 378/19, 98.8, 207, 208; 250/252.1  
See application file for complete search history.

(56) References Cited

U.S. PATENT DOCUMENTS

| 5,473,663 | A | * | 12/1995 | Hsieh | ............ 378/207 |
| 6,137,859 | A | | 10/2000 | Von Der Haar et al. | |
| 6,488,409 | B1 | * | 12/2002 | Vafi et al. | ............ 378/207 |
| 7,046,763 | B2 | * | 5/2006 | Hoffman | ............ 378/98.8 |

FOREIGN PATENT DOCUMENTS

DE    19811044 C1    4/1999

\* cited by examiner

*Primary Examiner*—Jurie Yun  
(74) *Attorney, Agent, or Firm*—Harness, Dickey & Pierce, P.L.C.

(57) ABSTRACT

A method is for testing the quality of a detector module for an x-ray computer tomograph. In order to achieve a quality test of detector modules, it is proposed in at least one embodiment, to fit a holding device with at least one reference detector module and with the detector module to be tested, and subsequently to evaluate both the reference signals supplied by the reference detector module and the test signals supplied by the detector module to be tested.

20 Claims, 1 Drawing Sheet

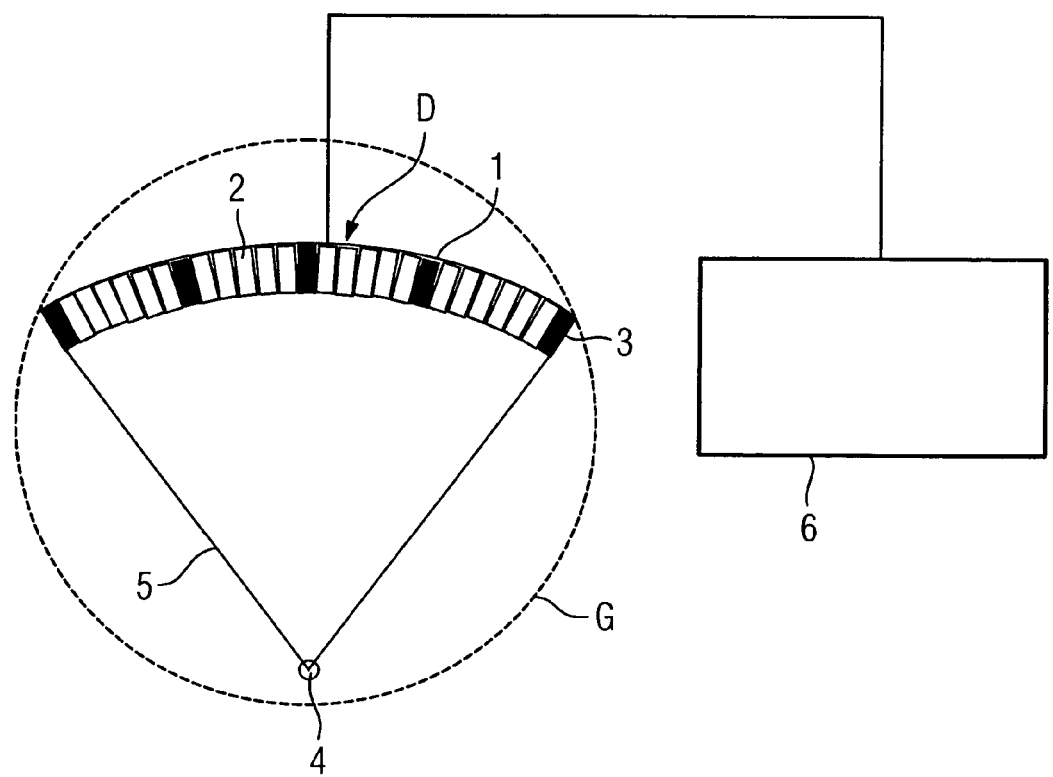

METHOD FOR TESTING THE QUALITY OF A DETECTOR MODULE FOR AN X-RAY COMPUTER TOMOGRAPH

The present application hereby claims priority under 35 U.S.C. §119 on German patent application number DE 10 2004 057 741.2 filed Nov. 30, 2004, the entire contents of which is hereby incorporated herein by reference.

FIELD

The invention generally relates to a method for testing the quality of a detector module for an x-ray computer tomograph and/or to the use of a test gantry corresponding to the gantry of the x-ray computer tomograph.

BACKGROUND

As a result of manufacturing, detector modules for a detector of an x-ray computer tomograph do not always exhibit identical imaging properties, that is to say in some circumstances they supply divergent signals when the same x-ray intensity is irradiated. When a detector is constructed by using detector modules whose properties exhibit an impermissibly high spread, this can have a negative influence on the quality of an image produced thereby.

With regard to this, the quality of the detector modules is tested in accordance with the prior art. The detector modules are usually mounted on a detector device. This is a frame of generally arcuate design and having a multiplicity of juxtaposed slots for connecting the detector modules. With regard to the quality of the detector module, it is possible to tolerate spreads of different intensity in the properties, depending on the position of a detector module on the detector device.

Detector modules with a large spread in their properties are usually mounted in the vicinity of the ends of the detector device, whereas detector modules with a low spread in their properties are mounted in the middle of the detector device.

In accordance with a first method according to the prior art, the detector device for holding detector modules is fitted completely with detector modules. Subsequently, the image quality that can be achieved with the detector is tested. If the image quality does not correspond to prescribed criteria, the arrangement of the detector modules is changed using the "try and error" principle until the desired image quality has been achieved. The known method is lengthy and requires the use of specially qualified staff. Apart from this, it is not possible to predict the time period for testing the image quality, and this disturbs the production cycle. Finally, it is possible with the aid of the known method for the quality of the detector modules used to be determined only relatively and not absolutely.

In accordance with a second method, known from DE 198 11 044 C2, the imaging properties of each detector module are tested before the production of the detector by using a special test station. The measurement results obtained in this case are then used with the aid of a special selection method to allocate the detector modules installation positions on the detector device. The provision of a special test station is costly. Moreover, there is a need, in turn, for specially trained staff to operate the special test station.

SUMMARY

It is an object of at least one embodiment of the invention to reduce or even eliminate at least one of the disadvantages according to the prior art. One aim of at least one embodiment, for example, is to specify a method that is simple and accurate, and to specify a method for testing the quality of detector modules for x-ray computer tomographs. According to a further aim of at least one embodiment of the invention, the intention is also thereby, inter alia, to enable an absolute determination of the quality of the tested detector module.

According to at least one embodiment of the invention, a method for testing the quality of a detector module for an x-ray computer tomography having the following steps is provided:

providing a measuring device including an x-ray source and a holding device which is equipped with at least one reference detector module and has at least one free space for inserting the detector module to be tested, inserting the detector module to be tested into the free space, irradiating a prescribed x-ray intensity distribution onto a detector comprising the reference detector module and the detector module to be tested, measuring the reference signals supplied by the reference detector module, and measuring the test signals supplied by the detector module to be tested, and evaluating the supplied signals.

The proposed method can be carried out relatively easily. It is particularly exact and timesaving. No specially experienced or trained expert staff are required. It is thereby possible, in particular, to acquire the suitability of the detector module for a specific installation position in the detector with reference to the x-ray source. There is no need to provide a special test station.

An absolute determination of the quality of the detector modules is possible as a consequence of the proposed use of reference detector modules. Defective detector modules can be identified at an early stage and rejected. A holding device in the meaning of the present invention is to be understood as including a frame or a carrier for holding the detector modules. It can be, for example, a frame that is bent in a φ-direction and serves as a component of a gantry of an x-ray computer tomograph. A reference detector module in the meaning of the present invention is understood to include a detector module whose properties correspond to defined prescribed criteria. These are selected detector modules that exhibit only slight deviations with regard to prescribed specified properties.

According to a particularly advantageous refinement of at least one embodiment, a test gantry corresponding to the gantry of the x-ray computer tomograph is used as a measuring device. It is thereby possible to keep the outlay on testing the quality of the detector modules particularly low. A mass-produced gantry can be used as measuring device.

Moreover, it is possible to use an electronic test device corresponding to the electronic device of the x-ray computer tomograph for measuring and processing the signals. The detector modules are therefore tested in the same system environment as when being used in the detector of the x-ray computer tomograph. The results obtained for the quality of the detector modules are particularly exact. It is possible, for example, to use as measuring device and electronic device a test x-ray computer tomograph corresponding to the x-ray computer tomograph. All that is required is to provide a special software for operating the electronic device or the hardware of the test x-ray computer tomograph.

According to a further refinement of at least one embodiment, the detector module to be tested is inserted between two reference detector modules. It is also possible to insert a number of detector modules between two reference detector modules in each case. A particularly exact measurement is possible given that the detector module(s) to be tested is/are held in each case between two reference detector modules. It is possible here, in particular, to determine the quality of the detector module when there is a dependence between the x-ray intensity and the spectral composition of the x radiation in a φ-direction.

In order to further simplify the method the holding device is not rotated during the measurement. It is thereby possible to dispense with fastening the detector element to be tested in a special way by means of fastening elements such as screws. It suffices simply to plug the detector element into a plug-in connector provided on the holding device, and thereby to produce a connection with the downstream electronic device.

At least one of the following reference parameters is advantageously determined from the reference signals: spectral linearity, signal drift, signal strength, persistence, temperature drift, z-gradient, current linearity. Particularly when a number of reference detector modules are used, the reference parameter can be determined by averaging. The averaging can be performed, for example, by interpolation or second or third degree. It is possible thereby to correct deviations in the signals supplied by the reference detectors or in the reference parameters resulting therefrom. However, the averaging can also be performed by another mathematical combination of a multiplicity of reference signals.

A test parameter corresponding to the reference parameter can be determined from the test signals. The evaluation can be performed by normalizing the test signals by using the reference signals and/or by normalizing the test parameters by use of the reference parameters corresponding thereto. This enables an absolute determination of the quality of the detector modules in a simple way.

According to a further refinement of at least one embodiment of the method, each normalized test signal and/or test parameter is assigned a value range. This enables the detector modules to be rejected and/or classified as a function of the quality determined. A tested detector module can be rejected when at least one of the normalized test signals and/or test parameters is outside the value range provided therefore. It is expedient for this purpose to take account of all the acquired normalized test signals and/or test parameters.

The unrejected detector modules can be classified with the aid of prescribed classification rules. It suffices to test a subset of the normalized test signals and/or test parameters. Using only a prescribed subset for classification contributes to speeding up at least one embodiment of the method. The classification of the detector modules can be performed, for example, by allocating each tested detector module a preferred installation position on the holding device. The classification can be performed using conventional classification methods such as are known, for example, from DE 198 11 044 C1, the entire contents of which is hereby incorporated herein by reference.

According to a further measure of at least one embodiment of the invention, it is provided to use test gantry, which corresponds to the gantry of an x-ray computer tomograph and is provided with at least one reference detector module, as measuring device for testing the quality of detector modules for the x-ray computer tomograph. The proposed use renders the provision of a special test station superfluous. It is possible to have recourse to a component of the x-ray computer tomograph that is mass-produced and therefore available at a relatively favorable price. There is no need to design and produce a special test station.

According to a particularly advantageous refinement of the use, an electronic test device corresponding to the electronic device of the x-ray computer tomograph is used for measuring and processing the signals supplied by the detector module to be tested. The proposed refinement can be implemented, for example, by using an x-ray computer tomograph that corresponds in terms of its design and hardware implementation to the x-ray computer tomograph for which the detector modules to be tested are provided.

BRIEF DESCRIPTION OF THE DRAWINGS

The invention is explained in more detail below by way of example with the aid of the single figure.

The figure generally illustrates a holding device with a multiplicity of slots for plugging in and connecting detector modules.

DETAILED DESCRIPTION OF THE EXAMPLE EMBODIMENTS

An arcuately designed holding device 1 with a multiplicity of slots 2 (shown schematically here) for plugging in and connecting detector modules is provided in the figure. Specific slots 2 are fitted with reference detector modules 3. An x-ray source 4 is provided opposite the detector device 1. An x-ray fan emanating therefrom is denoted by the reference numeral 5.

The apparatus shown is a test gantry G that, apart from the fitting of the detector device 1 with reference detector modules 3 or detector modules to be tested, is identical in construction to the gantry of the x-ray computer tomograph. A drive, usually provided thereon, for rotating the measuring device, formed from the detector D and the x-ray source 4 in a φ-direction can be omitted. The reference numeral 6 schematically denotes an electronic test device downstream of the detector G. This is expediently the hardware of an x-ray computer tomograph that is identical in construction to an x-ray computer tomograph for which the detector modules to be tested are provided.

The apparatus shown is used as follows for testing the quality of the detector modules:

The detector device 1 is fitted at the slots 2 with the detector modules to be tested (not shown in the figure). The detector D is subsequently irradiated with the aid of the x-ray source 4 with a prescribed x-ray intensity. The irradiation can be performed repeatedly for a prescribed time period.

The reference and test signals produced by the reference detector modules 2 and the detector modules are evaluated with the aid of the downstream electronic test device 6. For this purpose, a suitable software is used to determine the following reference parameters from the measured reference signals: spectral linearity, signal drift, signal strength, persistence, temperature drift, z-gradient. The reference parameters can be determined by averaging.

The test parameters are normalized for each detector module by using the transmitted reference parameters, formed by averaging, if appropriate. The normalized test parameters form absolute values with the aid of which the quality of the detector modules can be determined.

Subsequently, the normalized test parameters are used as a basis for classifying the detector modules, in a way known from DE 198 11 044 C1, for example. In the process, each detector module is allocated a preferred installation position on the holding device. The determined values are stored in a database. A suitable program can be used for automatically specifying a set of detector modules for constructing a detector, each detector module being allocated an installation position on the holding device of the detector D.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for testing the quality of a detector module for an x-ray computer tomography device, comprising:
   providing a measuring device including an x-ray source, and a holding device equipped with at least one reference detector module and including at least one free space for inserting the detector module to be tested;
   inserting the detector module to be tested into the free space;
   irradiating a prescribed x-ray intensity distribution onto a detector including the reference detector module and the detector module to be tested;
   measuring the reference signals supplied by the reference detector module, and measuring the test signals supplied by the detector module to be tested; and
   evaluating the supplied signals to determine the quality of the detector module.

2. The method as claimed in claim 1, wherein a test gantry corresponding to the gantry of the x-ray computer tomography device is used as a measuring device.

3. The method as claimed in claim 2, wherein an electronic test device corresponding to an electronic device of the x-ray computer tomography device is used for measuring and processing the signals.

4. The method as claimed in claim 2, wherein the detector module to be tested is inserted between two reference detector modules.

5. The method as claimed in claim 2, wherein the detector is not rotated during the measurement.

6. The method as claimed in claim 2, wherein at least one of the following reference parameters is determined from the reference signals: spectral linearity, signal drift, signal strength, persistence, temperature drift, z-gradient, and current linearity.

7. The method as claimed in claim 2, wherein a reference parameter is determined by averaging.

8. The method as claimed in claim 7, wherein a test parameter corresponding to the reference parameter is determined from the test signals.

9. The method as claimed in claim 1, wherein an electronic test device corresponding to an electronic device of the x-ray computer tomography device is used for measuring and processing the signals.

10. The method as claimed in claim 1, wherein the detector module to be tested is inserted between two reference detector modules.

11. The method as claimed in claim 1, wherein the detector is not rotated during the measurement.

12. The method as claimed in claim 1, wherein at least one of the following reference parameters is determined from the reference signals: spectral linearity, signal drift, signal strength, persistence, temperature drift, z-gradient, and current linearity.

13. The method as claimed in claim 1, wherein a reference parameter is determined by averaging.

14. The method as claimed in claim 13, wherein a test parameter corresponding to the reference parameter is determined from the test signals.

15. The method as claimed in claim 1, wherein the evaluation is performed by normalizing the test signals by at least one of the use of the reference signals and by normalizing test parameters by use of reference parameters corresponding thereto.

16. The method as claimed in claim 15, wherein each of the test parameters is assigned a value range.

17. The method as claimed in claim 1, wherein the tested detector module is rejected when at least one of a plurality of test parameters is outside a value range provided therefore.

18. The method as claimed in claim 1, wherein unrejected detector modules are classified with the aid of prescribed classification rules.

19. A method, comprising:
   testing the quality of detector modules for an x-ray computer tomography device using a test gantry of the x-ray computer tomography device as a measuring device, the x-ray tomography device having at least one reference detector module; wherein
   the testing using the test gantry includes,
   measuring reference signals supplied by the at least one reference detector module,
   measuring test signals supplied by one of the detector modules to be tested, and
   evaluating the supplied signals to determine the quality of the detector module.

20. The method as claimed in claim 19, wherein an electronic test device corresponding to an electronic device of the x-ray computer tomography device is used for measuring and processing the signals supplied by the detector module to be tested.

* * * * *